United States Patent
Fajnszajn

(10) Patent No.: US 7,044,939 B1
(45) Date of Patent: May 16, 2006

(54) MALE EXTERNAL CATHETER WITH INTEGRAL STRAP

(76) Inventor: Aleksander Fajnszajn, P.O. Box 6684, San Rafael, CA (US) 94903

( * ) Notice: Subject to any disclaimer, the term of this patent is extended or adjusted under 35 U.S.C. 154(b) by 0 days.

(21) Appl. No.: 09/397,405

(22) Filed: Sep. 16, 1999

Related U.S. Application Data

(63) Continuation-in-part of application No. 09/017,152, filed on Feb. 2, 1998.

(51) Int. Cl.
A61F 5/453 (2006.01)

(52) U.S. Cl. .................. 604/349; 604/346; 604/347; 604/351; 604/352; 604/353

(58) Field of Classification Search .............. 604/327, 604/346, 347, 349, 351, 352, 353; 4/144.3
See application file for complete search history.

(56) References Cited

U.S. PATENT DOCUMENTS

| | | | | | |
|---|---|---|---|---|---|
| 947,725 | A | * | 1/1910 | Yates | |
| 2,389,831 | A | * | 11/1945 | Welsh | 2/21 |
| 2,940,450 | A | * | 6/1960 | Witt et al. | 128/295 |
| 3,357,430 | A | * | 12/1967 | Rosenberg | 128/295 |
| 4,475,909 | A | * | 10/1984 | Eisenberg | 604/349 |
| 4,685,913 | A | * | 8/1987 | Austin | 604/349 |
| 4,769,020 | A | * | 9/1988 | Eaton | 604/352 |
| 4,798,600 | A | * | 1/1989 | Meadows | 604/347 |
| 4,971,074 | A | * | 11/1990 | Hrubetz | 128/885 |
| 5,009,649 | A | * | 4/1991 | Goulter et al. | 604/350 |
| 5,618,277 | A | * | 4/1997 | Goulter | 604/349 |
| 5,741,511 | A | * | 4/1998 | Lee et la. | 424/449 |
| 5,797,890 | A | * | 8/1998 | Goulter et al. | 604/351 |
| 5,855,206 | A | * | 1/1999 | Ireland | 5/95 |

FOREIGN PATENT DOCUMENTS

FR 1508356 * 1/1968

* cited by examiner

*Primary Examiner*—John G. Weiss
*Assistant Examiner*—Michael Bogart

(57) ABSTRACT

In a male external urinary catheter comprising a cylindrical discharge tube connected to a funnel through a bulbous zone wherein the extreme edge of the funnel is fitted with a rolled up coverette of latex rubber, polyurethane or the like that can be unfurled to encapsulate the patient's male organ, a unitary strap is provided having an connecting end unitary attached to said coverette and formed of a like material therewith and having intermediate and free end regions adapted to be looped about the coverette back upon themselves, the unitary strap including a fastener for attaching the strap upon itself without contacting the skin of a male patient.

1 Claim, 20 Drawing Sheets

MALE EXTERNAL CATHETER WITH INTEGRAL STRAP

RELATED APPLICATION

This is a continuation-in-part of Ser. No. 09/017,152 filed Feb. 2, 1998 for "MALE EXTERNAL CATHETER WITH UNITARY STRAP".

SCOPE OF THE INVENTION

This invention relates to a male external urinary catheter comprising a cylindrical discharge tube connected to a funnel through a bulbous zone wherein the extreme edge of the funnel is fitted with a rolled up coverette of latex rubber, polyurethane or the like that can be unfurled to encapsulate the patient's male organ, and more particularly to such a catheter in which the coverette is provided with an unitary strap integrally molded with respect to its base region wherein the unitary strap of a like material, defines a connecting end, an intermediate and a free end region.

In one aspect, the free end region is provided with an outer surface fitted with a loop element of a VELCRO fastener, where VELCRO is a required trademark. And the intermediate region of the unitary strap is provided with an inner surface fitted with the hook element of such fastener. The connecting end region can be the same width as the adjoining regions, or be of less width. In an activated state, the strap is looped about the base region of the unfurled coverette back upon itself wherein the hook and loop elements of the VELCRO fastener are united. The distance between adjoining edges of the hook and loop elements is smaller than the circumference of the maximum diameter of the funnel.

In another aspect, the free end and intermediate regions are provided with a series of openings parallel to the sides of the strap (each being of circular cross section) while the intermediate region is provided with a protuberance cantilevering from an outer surface thereof. And the connecting end of the unitary strap can be the same width as the adjoining regions, or be of less width. In an activated state, the strap is looped about the base region of the unfurled coverette back upon itself wherein the protuberance and one of the series of openings are united to form attachment therebetween. The distance between the protuberance and the closest adjoining opening is smaller than the circumference of the maximum diameter of the funnel.

In yet another aspect, the free end region is provided with an inner surface and with an outer surface opposite to the inner surface. The outer surface is fitted with a covered adhesive disc permanently attached thereto along a first broad surface of the latter. The disc also includes a second broad surface parallel to the first broad surface that is initially covered by a thin plastic cap to prevent activation of the underlying adhesive but which be peeled away in an activated stage to expose such adhesive. The connecting end region can be the same width as the adjoining regions, or be of less width. In an activated state, the strap is looped about the base region of the unfurled coverette back upon itself and after the thin plastic cap is removed, the underlying adhesive causes the unification of the inner and outer surfaces of the strap at a disconnectably connected joint. The distance between disc of adhesive and the location where the joint is formed is smaller than the circumference of the maximum diameter of the funnel.

In still yet another aspect, the thickness of the free end and intermediate regions are much reduced over that of the connecting end region. Reason: The connecting end region is unitarily formed with the coverette using three plys of material are provided. The center ply is formed as a single layer of polyvinyl chloride polymer in which top and bottom surfaces have been double polished to provide tackiness. The top and bottom plys are formed of latex rubber, polyurethane or the like. However, the free end and intermediate regions have the top and bottom plys stripped away thereby allowing them to disconnectably attach when brought into contact to form a disconnectably connected joint. Note that the connecting end of the unitary strap can be the same width as the adjoining regions, or be of less width. In an activated state, the strip is looped about the base region of the unfurled coverette back upon itself wherein specific regions of the top and bottom are brought into contact to form a disconnectably connected joint. The distance between end edge of the intermediate region and the location where the joint is formed is smaller than the circumference of the maximum diameter of the funnel.

BACKGROUND OF THE INVENTION

Male catheters of the prior art included the use of dual sided adhesive strips. Each strip, when activated, touched the skin of the patient. The duration of skin contact varied, including much of the day and/or night. When removed, irritation was an often occurrence.

SUMMARY OF THE INVENTION

The present invention relates to a male external urinary catheter comprising a cylindrical discharge tube connected to a funnel through a bulbous zone wherein the extreme edge of the funnel is fitted with a rolled up coverette of latex rubber, polyurethane or the like that can be unfurled to encapsulate the patient's male organ. In accordance with invention, the coverette of such a catheter is provided with an unitary strap that can be secured to the coverette without attachment of an adhesive to the skin of the patient. Such strap is preferably integrally molded with respect to the base region of the coverette and cantilevers therefrom for looping about same after deployment about the male organ. Means for attaching the strap upon itself, varies. Assuming the unitary strap of the invention always defines a connecting end, an intermediate and a free end region, the means for attachment can include one the following.

In one aspect, the free end region is provided with an outer surface fitted with a loop element of a VELCRO fastener. And the intermediate region of the unitary strap is provided with an inner surface fitted with the hook element of such fastener. The connecting end region can be the same width as the adjoining regions, or be of less width. In an activated state, the strap is looped about the base region of the unfurled coverette back upon itself wherein the hook and loop elements of the VELCRO fastener are united. The distance between adjoining edges of the hook and the loop elements is smaller than the circumference of the maximum diameter of the funnel.

In another aspect, the free end and intermediate regions are provided with a series of openings parallel to the sides of the strap (each being of circular cross section) while the intermediate region is provided with a protuberance cantilevering from an outer surface thereof. And the connecting end of the unitary strap can be the same width as the adjoining regions, or be of less width. In an activated state, the strap is looped about the base region of the unfurled coverette back upon itself wherein the protuberance and one of the series of openings are united to form attachment therebetween. The distance between the protuberance and the closest adjoining opening is smaller than the circumference of the maximum diameter of the funnel.

In yet another aspect, the free end region is provided with an inner surface and with an outer surface opposite to the inner surface. The outer surface is fitted with a covered adhesive disc permanently attached thereto along a first broad surface of the latter. The disc also includes a second broad surface parallel to the first broad surface that is initially covered by a thin plastic cap to prevent activation of the underlying adhesive but which be peeled away in an activated stage to expose such adhesive. The connecting end region can be the same width as the adjoining regions, or be of less width. In an activated state, the strap is looped about the base region of the unfurled coverette back upon itself and after the thin plastic cap is removed, the underlying adhesive causes the unification of the inner and outer surfaces of the strap at a disconnectably connected joint. The distance between disc of adhesive and the location where the joint is formed is smaller than the circumference of the maximum diameter of the funnel.

In still yet another aspect, the thickness of the free end and intermediate regions are much reduced over that of the connecting end region. Reason: The connecting end region is unitarily formed with the coverette using three plys of material are provided. The center ply is formed as a single layer of polyvinyl chloride polymer in which top and bottom surfaces have been double polished to provide tackiness. The top and bottom plys are formed of latex rubber, polyurethane or the like. However, the free end and intermediate regions have the top and bottom plys stripped away thereby allowing them to disconnectably attach when brought into contact to form a disconnectably connected joint. Note that the connecting end of the unitary strap can be the same width as the adjoining regions, or be of less width. In an activated state, the strap is looped about the base region of the unfurled coverette back upon itself wherein specific regions of the top and bottom are brought into contact to form a disconnectably connected joint. The distance between end edge of the intermediate region and the location where the joint is formed is smaller than the circumference of the maximum diameter of the funnel.

DETAILED DESCRIPTION OF THE INVENTION

Figure 1:
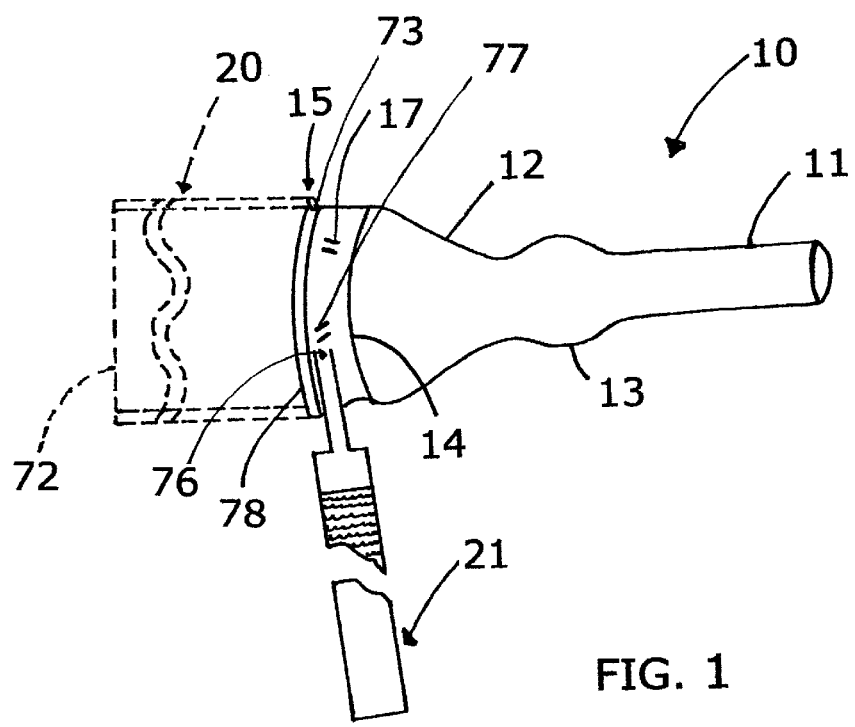
FIG. 1 is a perspective view of a male catheter incorporating the present invention.

FIG. 1 shows a male external urinary catheter 10. As indicated the catheter 10 comprises a cylindrical discharge tube 11 connected to a funnel 12 through a bulbous zone 13. The funnel 12 has an enlarged edge 14 of oval or circular cross section to which is attached a rolled up coverette 15. The coverette 15 is preferably formed of latex rubber, polyurethane or the like and functions as an encapsulator 20 after same is unfurled as shown. After the unfurling step is completed, the coverette 15 is provided with an unitary strap 21 that can secured the coverette 15 without attachment of an adhesive to the skin of the patient (not shown). Such strap 21 is preferably integrally molded with respect to the base region 17 of the coverette 15 and cantilevers therefrom for looping about same after deployment.

Means 25 for attaching the strap 21 upon itself, varies.

Figure 2:
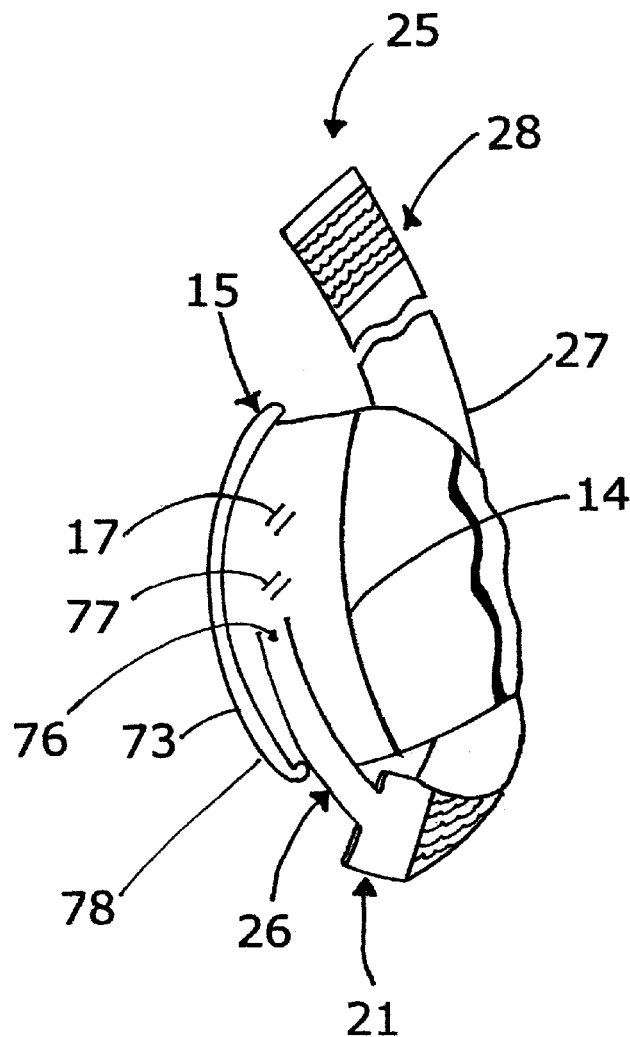
FIG. 2 is a fragmentary view of the catheter of FIG. 1 showing how an unitary strap of the invention can be folded back on itself.

As shown in FIG. 2, assuming the unitary strap 21 of the invention always defines a connecting end 26, an intermediate and a free end region 27, 28, the means 25 can include one the following.

Figure 3:
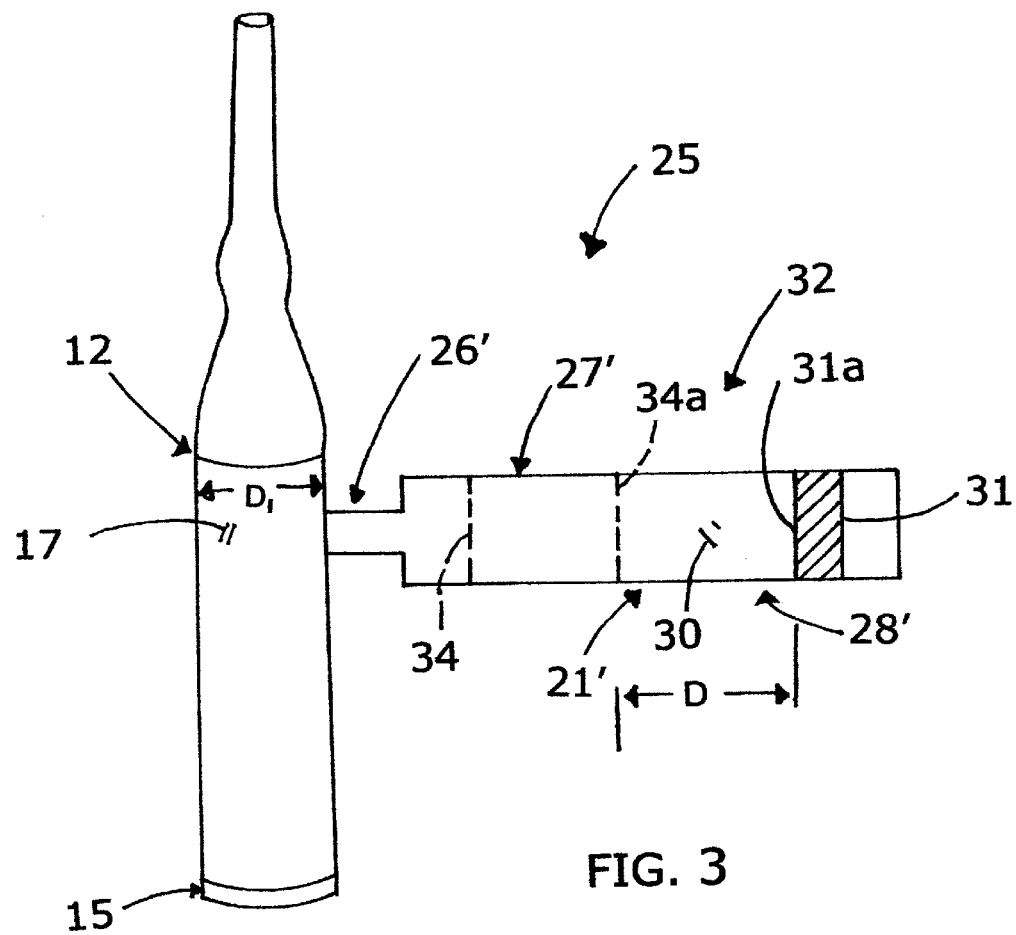
FIG. 3 is a front view of the male catheter of FIGS. 1 and 2 wherein the strap is shown in an extended position.
Figure 4:
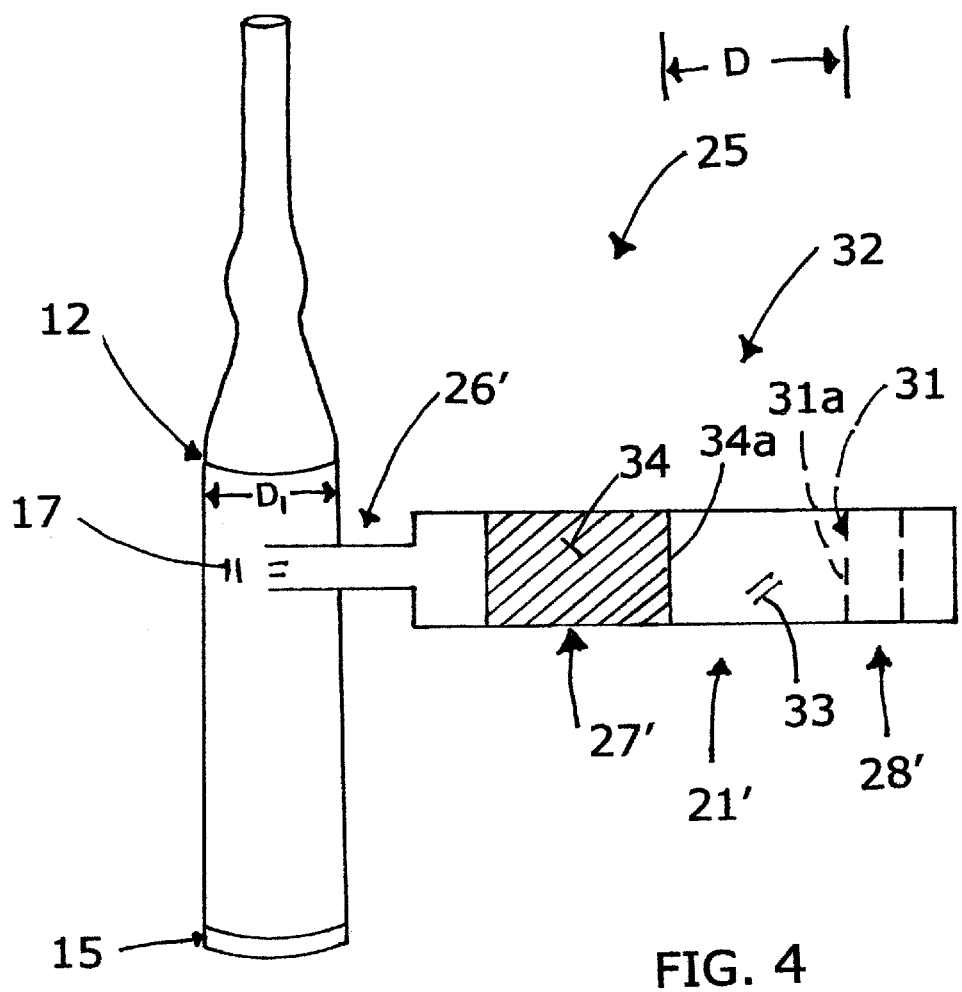
FIG. 4 is a back view of the male catheter of FIGS. 1 and 2 wherein the strap is shown in an extended position.
Figure 5:
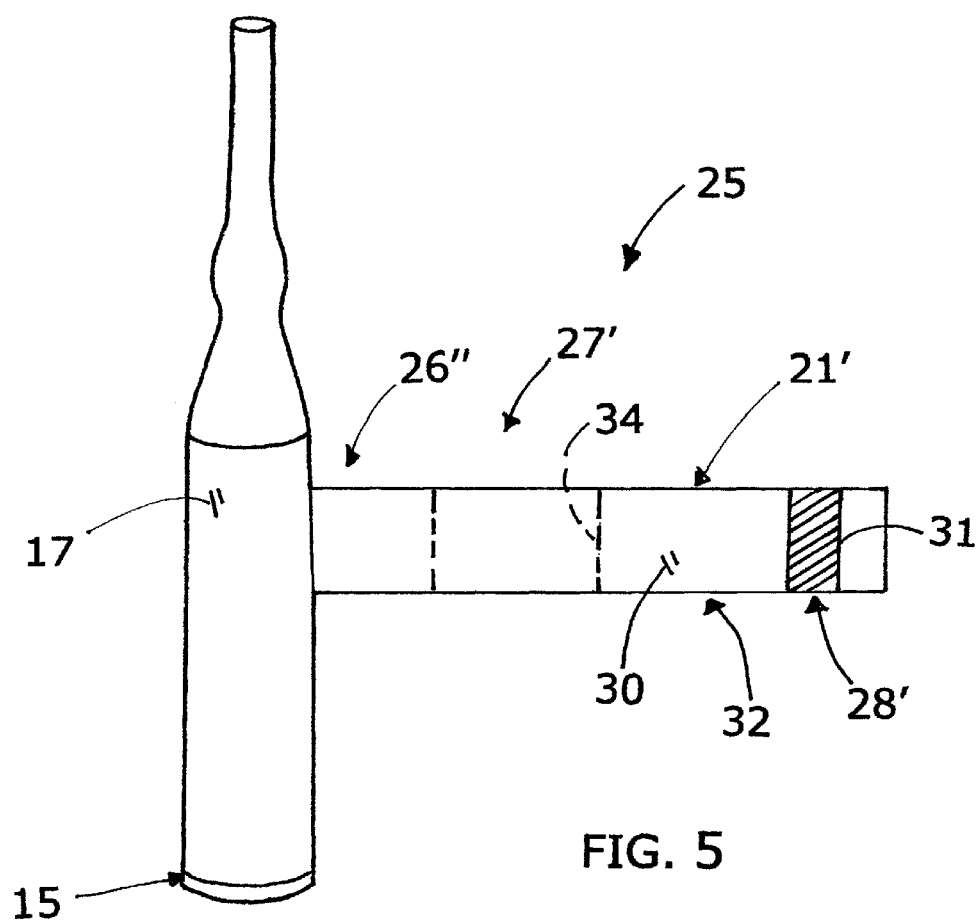
FIG. 5 is a front view of an alternative to the male catheter of FIGS. 1–4.
Figure 6:
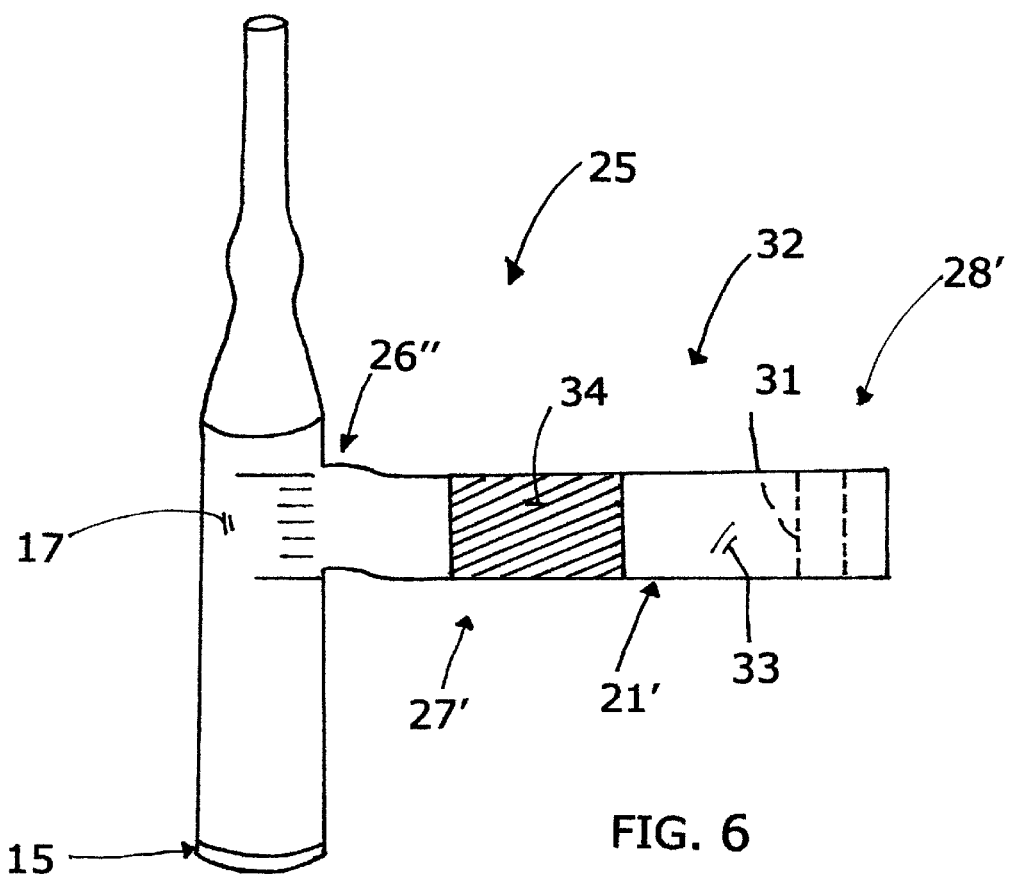
FIG. 6 is a back view of an alternative to the male catheter of FIGS. 1–4.

(1) As shown in FIGS. 3 and 4, the free end region 28' can be provided with an outer surface 30 fitted with a loop element 31 of a VELCRO fastener 32. And the intermediate region 27' of the unitary strap 21' is provided with an inner surface 33 fitted with the hook element 34 of such fastener 32. The connecting end region 26' can be of less width than the adjoining regions 27', 28', or be of the same width, see FIGS. 5 and 6 showing end region 26" that is the same width as the intermediate and end regions 27', 28'. Returning to FIGS. 3 and 4, in an activated state, the strap 21' is looped about the base region 17 of the unfurled coverette 15 back upon itself wherein the loop and hook elements 31, 34 of the VELCRO fastener 32 are united. The distance D between adjoining edges 31a, 34a of the loop element 31 and the loop element 34 is smaller than the circumference of the maximum diameter D1 of the funnel 12.

Figure 7:
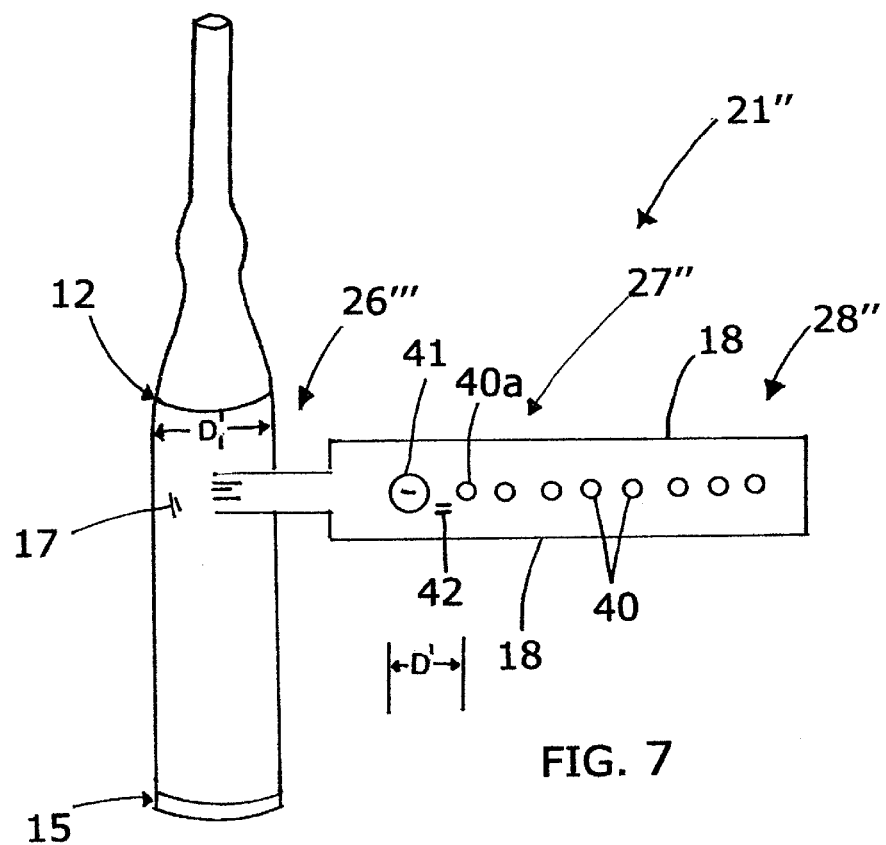
FIG. 7 is a front view akin to FIG. 3 showing another embodiment of the invention.
Figure 8:
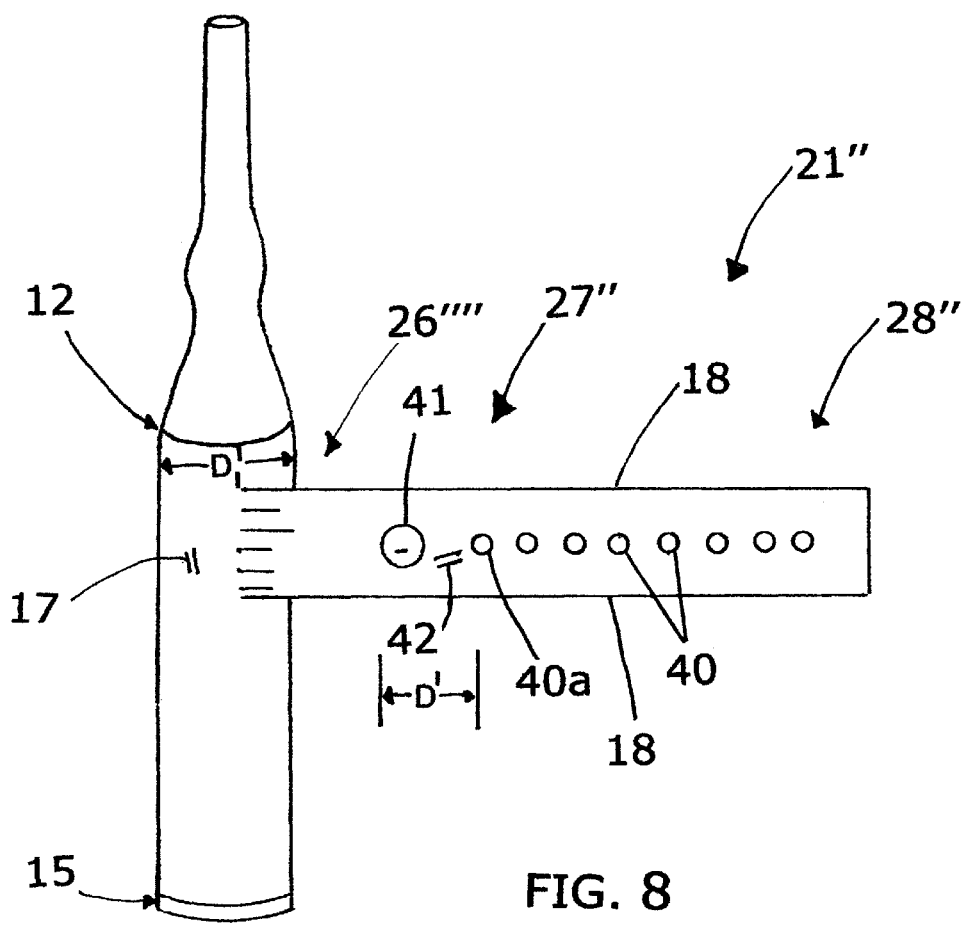
FIG. 8 is a back view akin to FIG. 4 showing another embodiment of the invention.

(2) As shown in FIGS. 7 and 8, the intermediate and free end regions 27", 28" are provided with a series of openings 40 parallel to sides 18 of the strap 21" (each being of circular cross section) while the intermediate region 27" is provided with a protuberance 41 cantilevering from an outer surface 42 thereof. And the connecting end region 26''' of FIG. 7 or end region 26'''' of FIG. 8 of the unitary strap 21" can be of a less width as the adjoining regions 27", 28", or be of the same width.

In an activated state, the strap 21" is looped about the base region 17 of the unfurled coverette 15 back upon itself wherein the protuberance 41 and one of the series of openings 40 are united to form attachment therebetween. The distance D' between the protuberance 41 and the closest adjoining opening 40a is smaller than the circumference of the maximum diameter D1' of the funnel 12.

Figure 9:
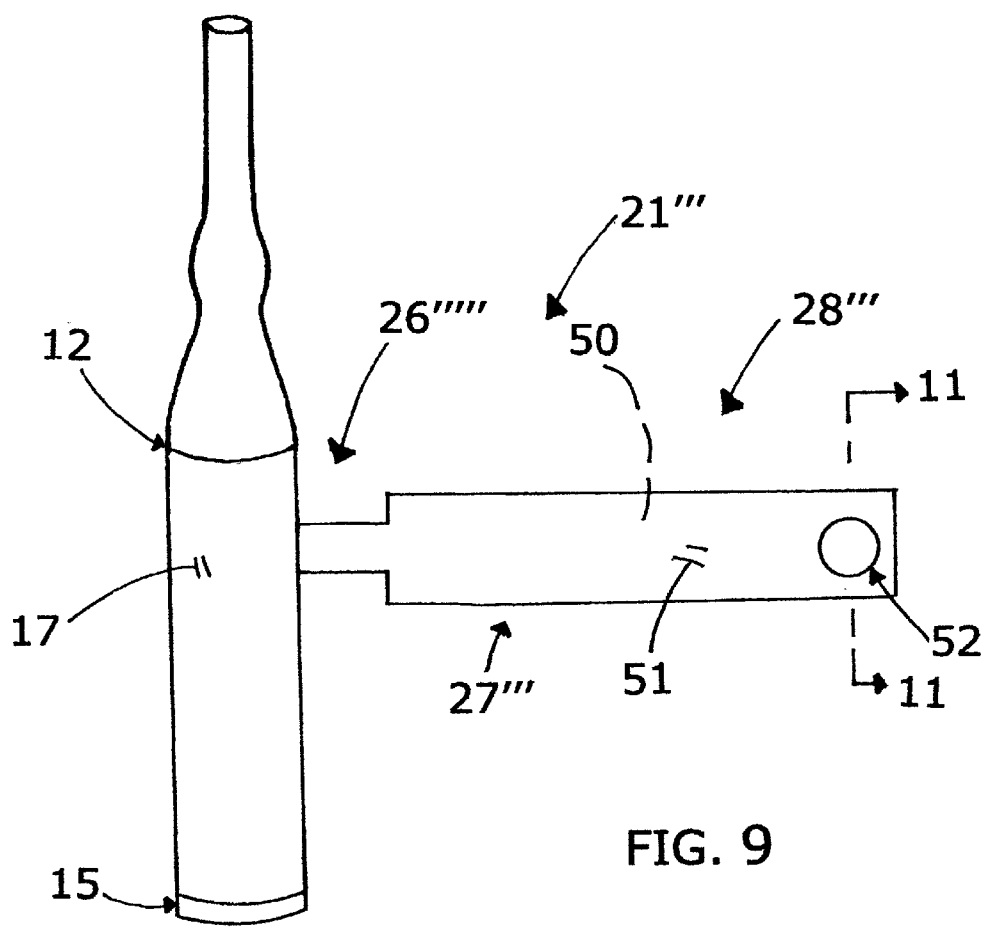
FIG. 9 is a front view showing still another embodiment of the invention.
Figure 10:
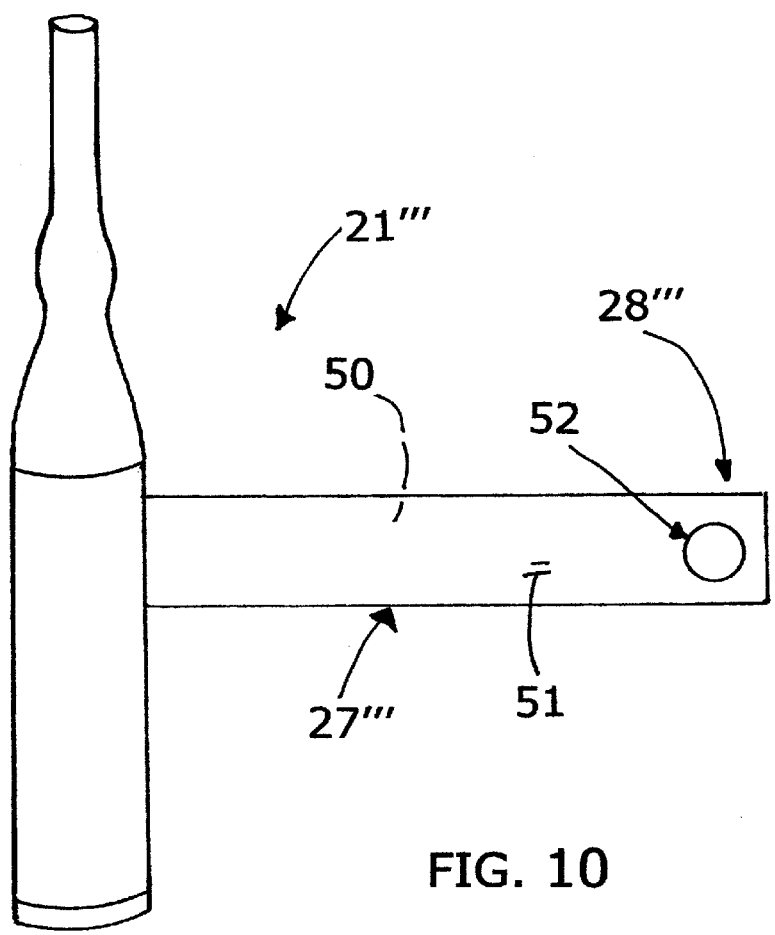
FIG. 10 is a back view showing still another embodiment of the invention.
Figure 11:
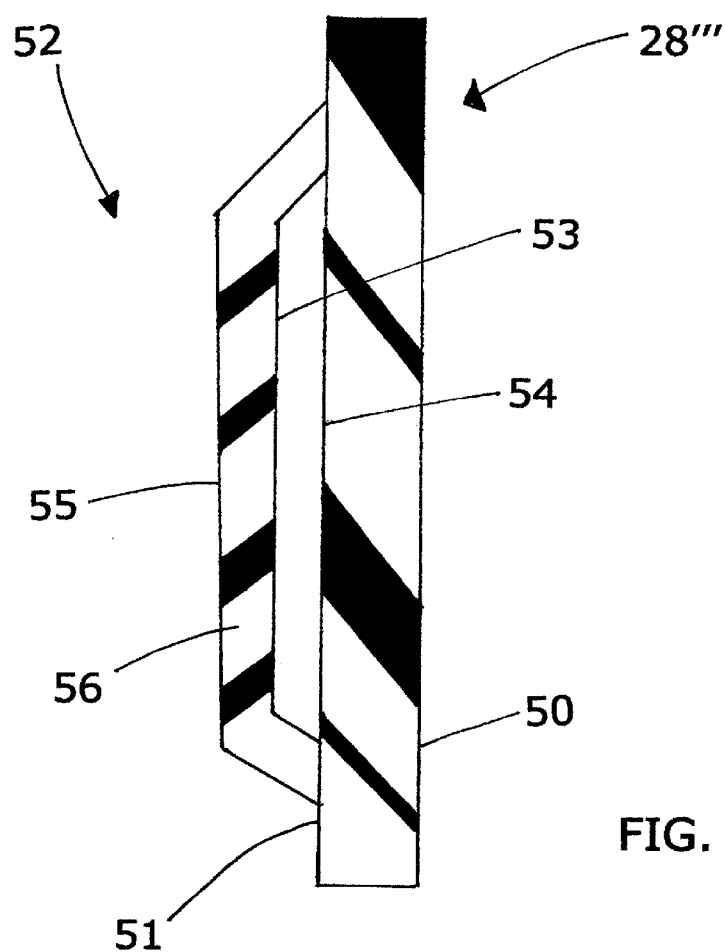
FIG. 11 is a section taken along line 11—11 of FIG. 9.
Figure 12:
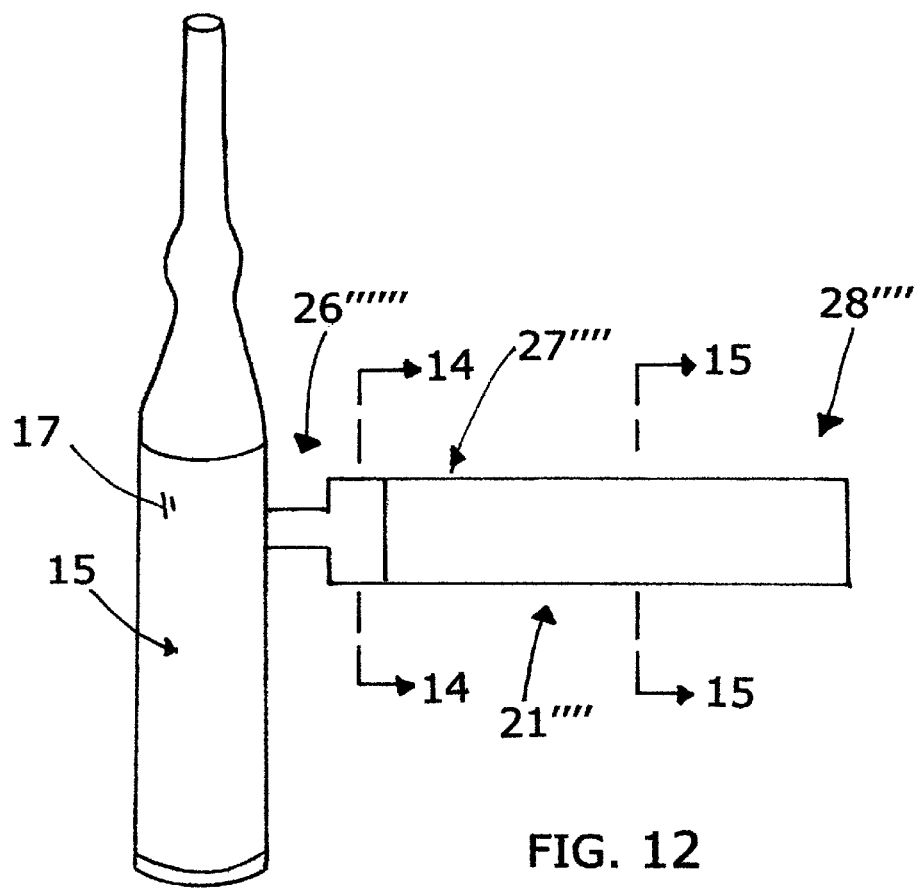
FIG. 12 is a front view of yet still another embodiment of the invention.
Figure 13:
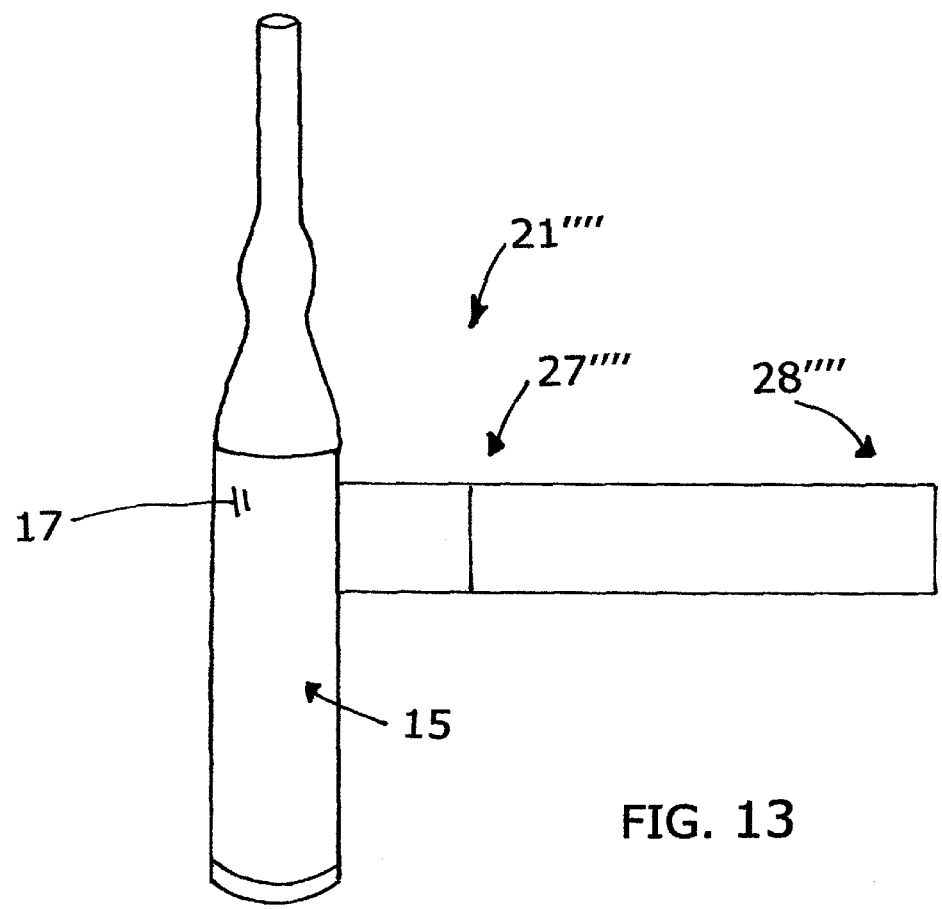
FIG. 13 is a back view of yet still another embodiment of the invention.
Figure 14:
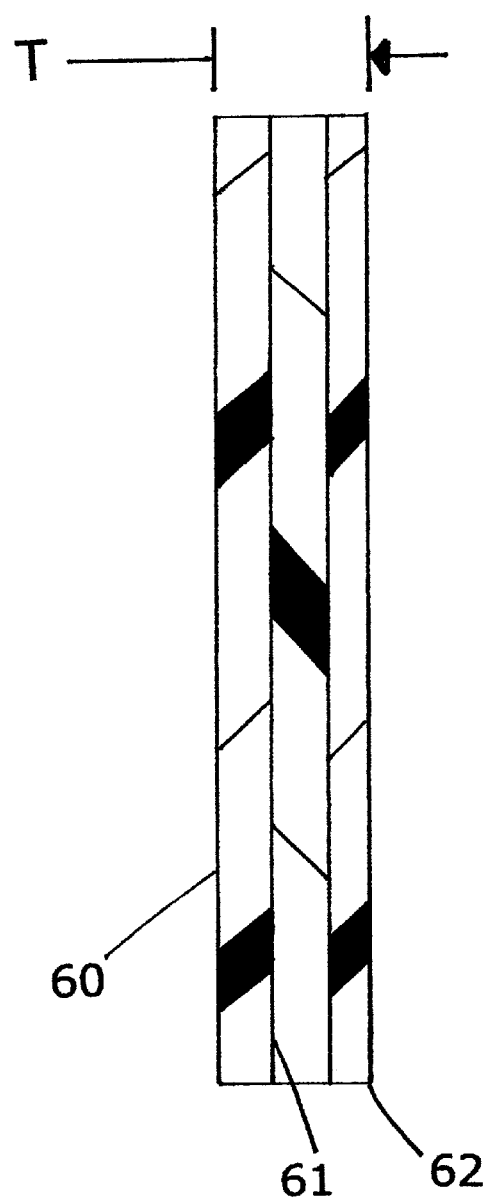
FIG. 14 is a section taken along line 14—14 of FIG. 12.

(3) As shown in FIGS. 9 and 10, the free end region 28''' is provided with an inner surface 50 and with an outer surface 51 opposite to the inner surface 50. The outer surface 51 is fitted with a covered adhesive disc means 52 permanently attached thereto, see FIG. 11. The disc means 52 includes a first broad surface 53 parallel to a second broad surface 54, the former being initially covered by a thin plastic cap 55 to prevent activation of the underlying adhesive 56 but which be peeled away in an activated stage to expose such adhesive 56. The connecting end region 26'''' can be of a less width than the adjoining regions 27''', 28''', or be of the same width, see FIG. 10. In an activated state, the strap 21''' is looped about the base region 17 of the unfurled coverette 15 back upon itself and after the thin plastic cap 55 is removed, the underlying adhesive 56 causes the unification of the inner and outer surfaces 50, 51 of the strap 21'''.

Figure 15:
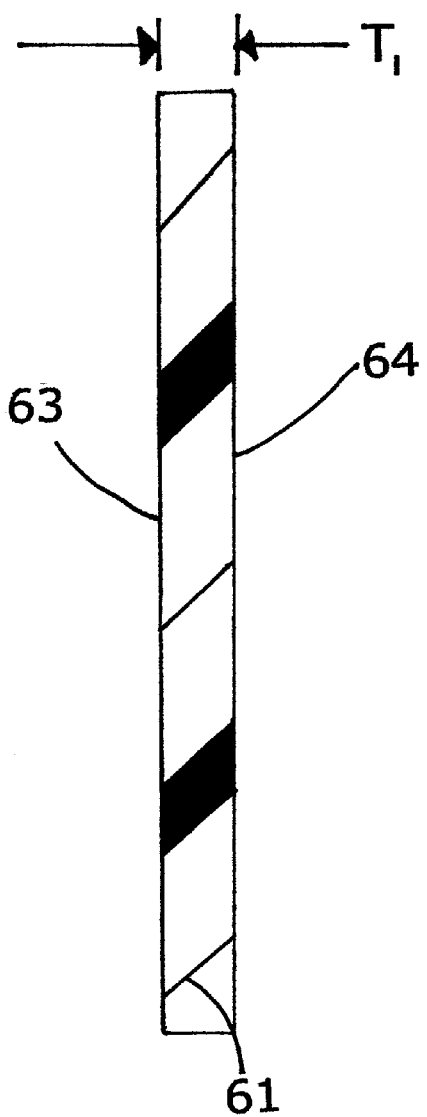
FIG. 15 is a section taken along line 15—15 of FIG. 12.

(4) As shown in FIGS. 12, 13, 14 and 15, the thickness T1 of the intermediate and free end regions 27'''', 28'''', see FIG. 15, is much reduced over the thickness T of the connecting end region 26''''. Reason: The connecting end region 26'''' as well as an adjacent portion of the intermediate region 27'''', are unitarily formed of same material as that of the coverette 15, viz., using three plys of material are provided, viz., plys 60, 61, 62, see FIG. 14. As shown in FIG. 15, the center ply 61 is formed of polyvinyl chloride polymer in which top and bottom surfaces 63, 64 have been double polished to provide tackiness. The top and bottom plys 60, 62 are formed of latex rubber, polyurethane or the like. However, the intermediate and free end regions 27'''', 28'''' have the top and bottom plys 60, 62 stripped away thereby allowing the center ply 61 to be disconnectably attached to itself when the strap 21'''' is activated. Note that the connecting end region 26'''' of the integral strap 21'''' can be less width than the adjoining regions 27'''', 28'''', or be of the same width, see FIG. 13.

In an activated state, the strap 21'''' is looped about the base region 17 of the unfurled coverette 15 back upon itself wherein specific regions of the top and bottom surfaces 63, 64 of the center ply 61 are brought into disconnectable contact.

It is obvious that alternate embodiments of the invention are suggestible to those skilled in the art from the discussion set forth above and such changes, modifications and alternatives are to be the scope of the invention as claimed below.

FURTHER EXPLANATION

Advantages of the invention will be made further apparent by a further definition of the terms "unitary or integral", "less width" (as provided for connecting end 26', 26'', 26'''') and "reuse" of the strap 21 by the original usee.

Figure 16:
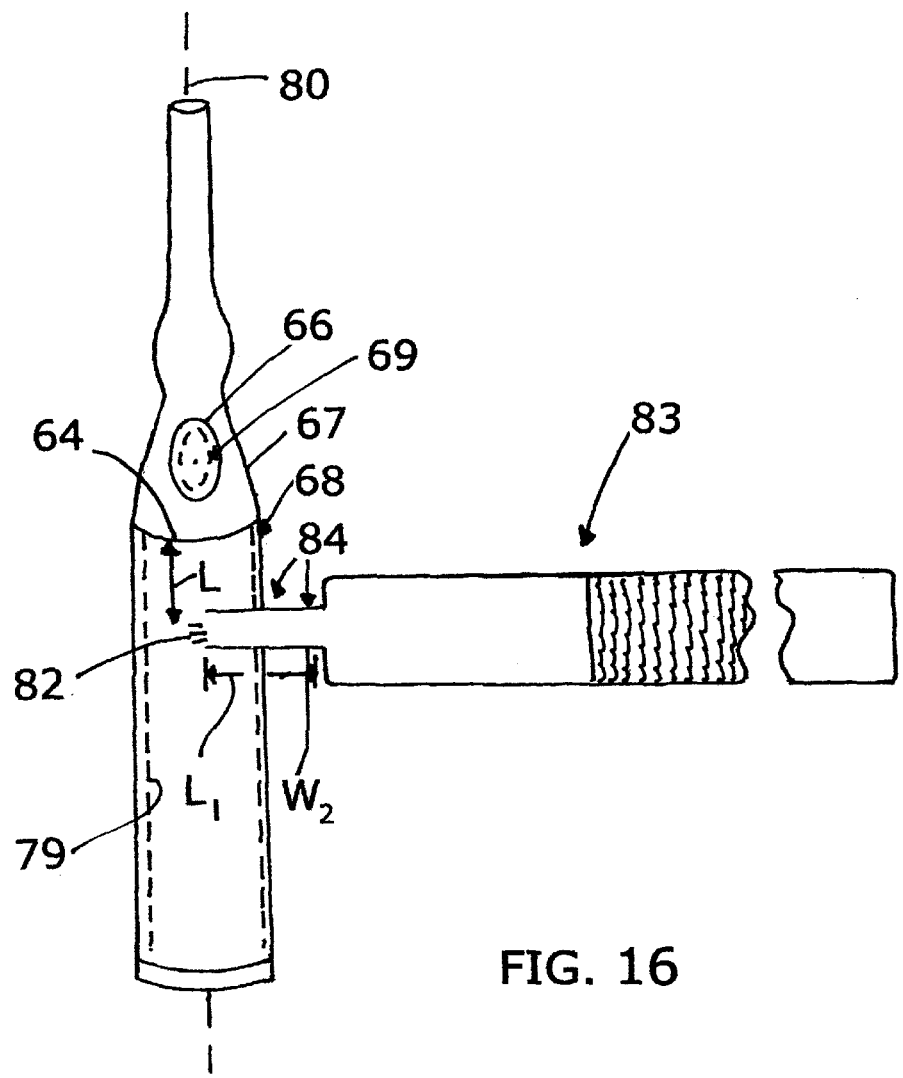
FIG. 16 is a front view showing still another embodiment of the invention.

By the term "unitary or integral", the male external urinary catheter 10 includes the following elements which are formed as a single unit such as by molding: at least the coverette 15 and strap 21 while the discharge tube 11, funnel 12, bulbous zone 13 can be themselves integrally formed and then attached to the coverette 15 along elongated edge 14. After being formed as a single unit, note that the coverette 15 and strap 21 can undergo further manufacturing processes:

(1) in FIGS. 3 and 4, a VELCRO fastener 32 can be provided wherein at end region 28, outer surface 30 fitted with loop element 31 of such VELCRO fastener 32 and wherein at intermediate region 27', inner surface 33 is fitted with the hook element 34 of such fastener 32;

(2) in FIGS. 7 and 8, series of openings 40 can be placed through intermediate and free end regions 27'', 28'' of the strap 21'' (each being of circular cross section) while intermediate region 27'' is provided with a protuberance 41 cantilevering from an outer surface 42 thereof;

(3) in FIGS. 9 and 10, disc means 52 can be added to free end region 28''' of the strap ''', namely at outer surface 51;

(4) in FIGS. 12, 13, 14 and 15, the reduced thickness T of the connecting end region 26'''' as well of an adjacent portion of the intermediate region 27'''' is provided by stripping off ply 60 and 62 associated with the intermediate and free end regions 27'''', 28'''', see FIG. 15; and (5) in FIG. 16, a vent 69 (shown covered by adhesive disc 66) is formed in funnel 67 forward of coverette 68, for the purpose of allowing easy transference of urine as taught and claimed in U.S. Pat. No. 4,656,675 issued Apr. 14, 1987 for "VENTED URINARY DRAINAGE DEVICE" incorporated herein by reference.

By the term "reduced width" as used in the description of connecting end 84 of strap 83 of FIG. 16, it is meant that the such width W2 is necessary to provide for making and packaging of the invention for latter use.

Note in FIGS. 1 and 2, that coverette 15 must be rolled back upon itself as a packaging step at a remote manufacturing site before being unfurled at a use site. To achieve the packaging step, the manufacturer first starts at open end 72 of the coverette 15 and then rolls the latter back upon itself to create circular increments 73. Note that the roll-up packaging step terminates when circular increments 73 are positioned as close as possible to integral connecting zone 76 (of the strap 21 and a portion 77 of the coverette 15). Result: a furled configuration 78 closely positioned adjacent to the enlarged edge 14 of the funnel 12 as shown, is easily achieved. Because of the reduced width W of connecting zone 26 of the strap 21, the furled configuration 78 is positioned closely adjacent to enlarged edge 14 of the funnel 12. Hence unfurling of the circular increments 73 about a patient's male organ (not shown) at the use site, is enhanced since the unfurling operation can start adjacent to the end of the patient's male organ (not shown) and then easily rolled forward.

Figure 17:
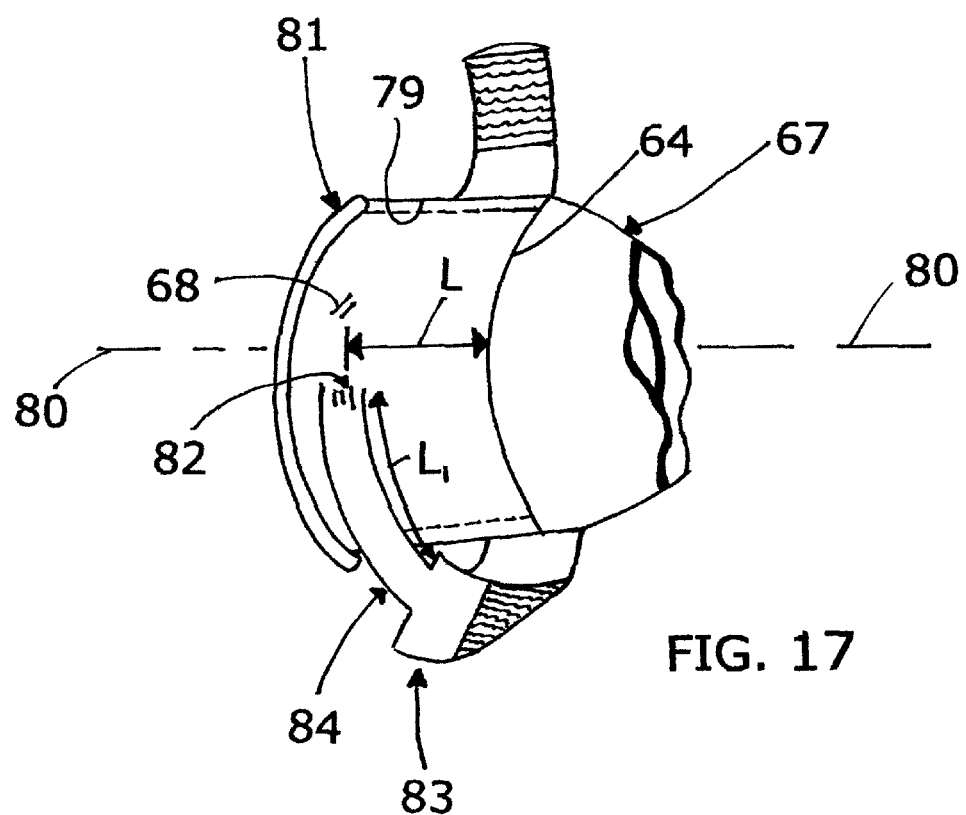
FIG. 17 is a detail of the embodiment of FIG. 16 showing inversion of the side wall and rolling up upon itself.
Figure 18:
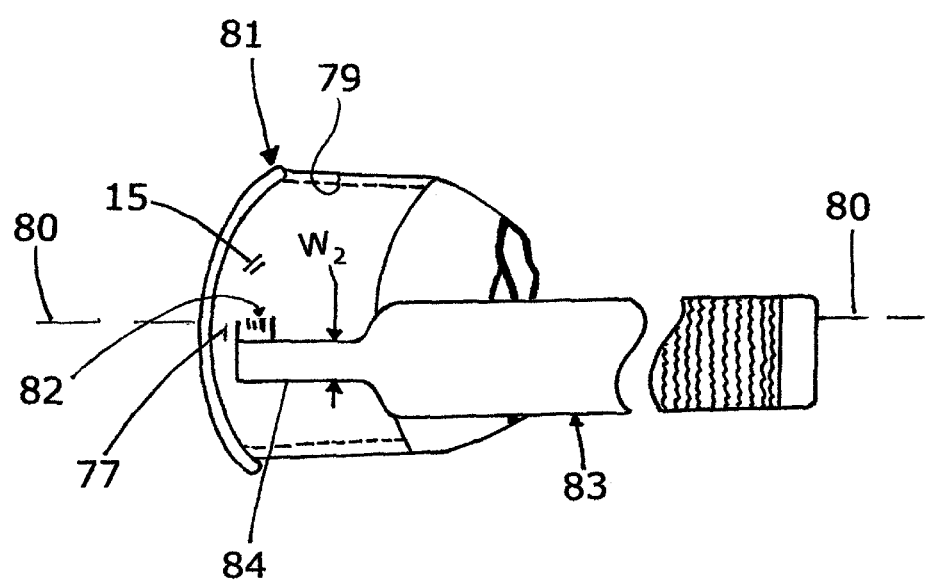
FIG. 18 is a further detail of the inversion of FIG. 17.
Figure 19:
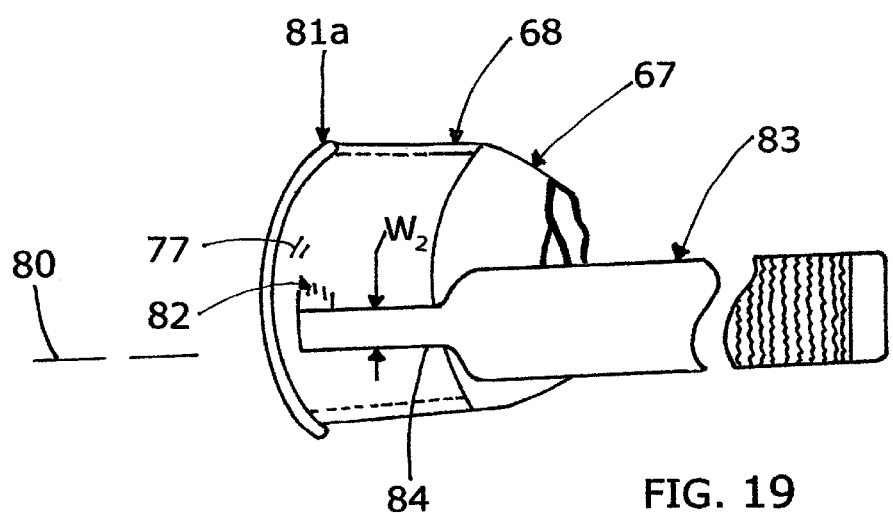
FIG. 19 is a still further detail of the inversion of FIG. 17.
Figure 20:
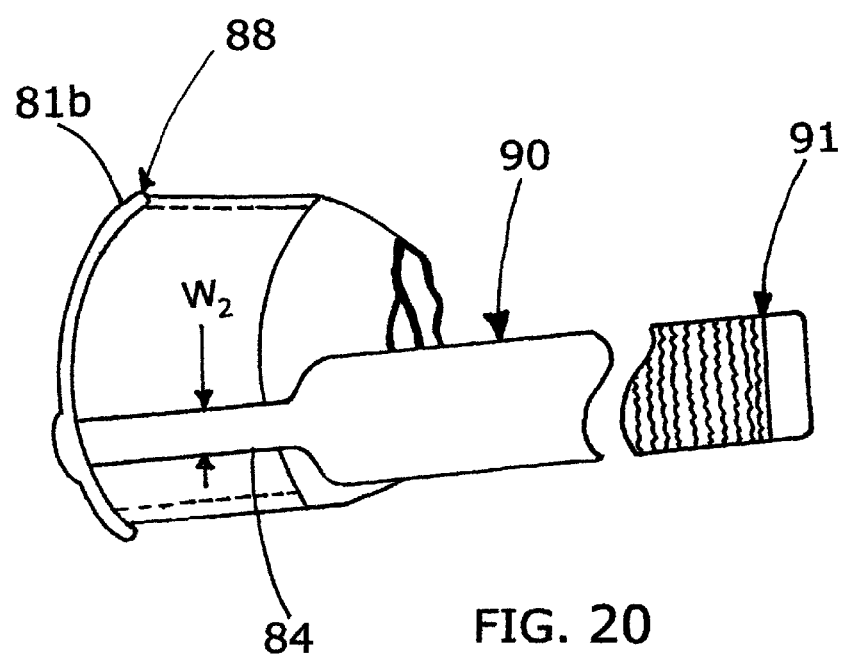
FIG. 20 is a yet still further detail of the inversion.

With reference to FIG. 16, note that prior to the packaging step (related to inverting side wall 79 of the coverette 68 back upon itself), the side wall 79 is concentric of axis of symmetry 80. But after inversion has occurred, see FIG. 17, such side wall 79 has been collapsed unto itself to form circular increments 81 with such increments 81 being capable of being rolled toward integral connecting zone 82, such zone 82 being formed between strap 83 and portion 77 of the coverette 15. Note in FIG. 18 that further progression of the circular increments 81 leads to the situation where the strap 83 is reoriented to a positioned more parallel to axis of symmetry 80 than as pictured in FIGS. 16 and 17. Note that the reduced width W2 of the connecting end 84 permits the strap 83 to be reoriented as shown, viz., so that the strap 83 can be positioned more parallel to axis of symmetry 80 than as pictured in FIG. 16. Note further in FIG. 19 that still further progression leads to the occurrence of an individual increment 81a becoming directly associated with the integral connecting zone 82 of strap 83 and coverette 15 and wherein the reduced width W2 of the connecting end 84 permits the connecting end 84 of the strap 83 reoriented as shown, to be further rolled into and become a part of the increment 81a. That is to say, the connecting end 84 is provided with sufficient flexibility to allow such reorientation and in-rolling. Returning now to FIG. 16, note that the length L between (i) longitudinal plane P—P bisecting the connecting zone 82 (and the strap 83) and (ii) enlarged edge 64 of the funnel 67, is less than length L1 defining the connecting end 84 to accommodate such in-rolling. That is, such reorientation permits the connecting end 84 to easily rolled forward over the connecting zone 82 until final increment 81b of furled configuration 88 is formed as shown in FIG. 20. This condition would not be possible if the width of such connecting end 84 was as wide as intermediate and free end regions 90, 91, i.e. there would not be sufficient flexibility afforded by such a condition.

By the term "reuse", it is meant that the user can adjust the fitting pressure applied by the adjusting means 25 of the strap 21 of FIGS. 1 and 2 after deployment. I.e., after an initial position has occurred by the attachment of the strap 21 back upon itself, the diameter of the patient's male organ underlaying the coverette 15 may change. Experience has shown that the strap 21 can then be readily adjusted by the user to maintain a suitably (and agreeable) attachment pressure to maintain correct positioning of the catheter 10.

That is to say, the strap 21 is not to be detached or separated from the coverette 15 during such adjustment sequence. It is integrally formed therewith. The strap 21 is merely adjustable but remains permanently attached and integrally formed with respect to the coverette 15.

What is claimed is:

1. In a male external urinary catheter comprising a cylindrical discharge tube connected to a funnel through a bulbous zone wherein the extreme edge of the funnel is fitted with a rolled up coverette that can be unfurled to encapsulate the patient's male organ, the improvement comprising a unitarily strap having an connecting end unitary attached to said coverette and formed of a like material therewith and having intermediate and free end regions adapted to be looped about said coverette back upon segments of themselves with co-extensive overlap of widths thereof, said unitary strap including non-adhesive means for attaching said strap upon itself without contacting skin of a male patient whereby said non-adhesive means can be easily detached and re-attached so that attaching pressure said strap relative to said patient's male organ can be adjusted, said means for attaching said strap back upon itself including a stripped-away central ply of polyvinyl chloride polymer in which top and bottom surfaces have been double polished to provide tackiness comprising said free end and intermediate regions, said connecting end region including three sandwished plys unitarily formed with respect to said coverette in which a central ply thereof is polyvinyl chloride polymer, said connecting end region being of a less width than that of said intermediate and free end regions easy furling and unfurling of said coverette and integral strap is provided.

* * * * *